(12) United States Patent
Jung et al.

(10) Patent No.: US 10,441,545 B2
(45) Date of Patent: Oct. 15, 2019

(54) MICROCELLULAR MICROSTRUCTURE AND METHOD FOR MANUFACTURING SAME

(71) Applicant: INDUSTRY-ACADEMIC COOPERATION FOUNDATION, YONSEI UNIVERSITY, Seoul (KR)

(72) Inventors: Hyung Il Jung, Seoul (KR); Su Yong Kim, Seoul (KR); Hui Suk Yang, Seoul (KR)

(73) Assignee: JUVIC INC., Seoul (KR)

( * ) Notice: Subject to any disclaimer, the term of this patent is extended or adjusted under 35 U.S.C. 154(b) by 0 days.

(21) Appl. No.: 15/536,586

(22) PCT Filed: Dec. 16, 2015

(86) PCT No.: PCT/KR2015/013826
§ 371 (c)(1),
(2) Date: Jun. 15, 2017

(87) PCT Pub. No.: WO2016/099159
PCT Pub. Date: Jun. 23, 2016

(65) Prior Publication Data
US 2017/0354610 A1 Dec. 14, 2017

(30) Foreign Application Priority Data
Dec. 16, 2014 (KR) .................. 10-2014-0181796

(51) Int. Cl.
*A61K 9/00* (2006.01)
*A61M 37/00* (2006.01)
*A61K 9/50* (2006.01)
*A61M 31/00* (2006.01)

(52) U.S. Cl.
CPC .......... *A61K 9/5005* (2013.01); *A61K 9/0021* (2013.01); *A61K 9/5089* (2013.01); *A61M 37/00* (2013.01); *A61M 37/0015* (2013.01); *A61M 31/002* (2013.01); *A61M 2037/0053* (2013.01)

(58) Field of Classification Search
None
See application file for complete search history.

(56) References Cited

U.S. PATENT DOCUMENTS

| | | | |
|---|---|---|---|
| 9,943,674 B2 * | 4/2018 | Jung | A61M 37/0015 |
| 2002/0082543 A1 * | 6/2002 | Park | A61B 5/1411 604/21 |
| 2005/0175670 A1 * | 8/2005 | Aoyagi | A61K 9/0024 424/426 |
| 2008/0269685 A1 | 10/2008 | Singh et al. | |
| 2016/0067469 A1 * | 3/2016 | Jung | A61M 37/0015 604/46 |
| 2018/0056053 A1 * | 3/2018 | Jung | A61M 37/0015 |

FOREIGN PATENT DOCUMENTS

| | | |
|---|---|---|
| KR | 10-2004-0105811 | 12/2004 |
| KR | 10-2006-0068513 | 1/2008 |
| KR | 10-2008-0050580 | 6/2008 |
| KR | 2010-0038071 | 4/2010 |
| KR | 10-2012-0006293 | 1/2012 |
| KR | 10-2014-0078644 | 6/2014 |
| KR | 2014-0105397 | 9/2014 |
| KR | 2014-0131879 | 11/2014 |
| KR | 2015-0072107 | 6/2015 |

OTHER PUBLICATIONS

Tan et al., Journal of Controlled Release, 88, pp. 215-228. (Year: 2003).*
Chen et al., "Epidermal immunization by a needle-free powder delivery technology: Immunogenicity of influenza vaccine and protection in mice," *Nature Medicine*, 2000; 6:1187-1190.
Donnelly et al., "Optical coherence tomography is a valuable tool in the study of the effects of microneedle geometry on skin penetration characteristics and in-skin dissolution," *Journal of Controlled Release*, 2010; 147: 333-341.
International Search Report and Written Opinion issued in Application No. PCT/KR2015/013826, dated May 4, 2016 (English translation provided).
Kim et al., "Novel cosmetic patches for wrinkle improvement: retinyl retinoate—and ascorbic acid-loading dissolving microneedles," *Int. J. Cosmet. Sci.* 2014; 36(3): 207-212.
Lee et al., "Drawing lithography for microneedles: A review of fundamentals and biomedical applications," *Biomaterials*, 2012; 33: 7309-7326 .
Park et al., "Biodegradable Polymer Microneedles: Fabrication, Mechanics, and Transdermal Drug Delivery," *Journal of Controlled Release*, 2005; 104: 51-66.

* cited by examiner

*Primary Examiner* — Abigail Vanhorn
(74) *Attorney, Agent, or Firm* — Norton Rose Fulbright US LLP

(57) ABSTRACT

The present invention relates to a microcontainer microstructure including a microcontainer film structure having a sharp tip portion and a method of manufacturing the same.

10 Claims, 18 Drawing Sheets

(a)

(b)

(c)

(d)

(a)

(b)

(c)

(d)

MICROCELLULAR MICROSTRUCTURE AND METHOD FOR MANUFACTURING SAME

CROSS-REFERENCE TO RELATED APPLICATIONS

This application is a national phase application under 35 U.S.C. § 371 of International Application No. PCT/KR2015/013826, filed Dec. 16, 2015, which claims priority to Korean Patent Application No. 10-2014-0181796, filed Dec. 16, 2014. The contents of the referenced applications are incorporated into the present application by reference.

TECHNICAL FIELD

The present invention relates to a microcontainer microstructure and a method of manufacturing the same.

BACKGROUND ART

A transdermal drug delivery system is a type of drug delivery system that delivers drugs through the skin, and is characterized by long duration and its ability to contain a large amount of drugs compared to other drug delivery systems such as oral administration agents, inhalants, injections, and the like. A first-generation transdermal drug delivery system is a patch-type product including a smoking cessation patch (nicotine patch), an inflammation treatment patch (Ketotop), a sickness patch (Kimite), a pain relief patch (pas), and the like, and is in a patch form with a drug applied thereon. This system operates under a principle that a drug acts locally or systemically through the skin, but it has a limitation in delivery in that only small-molecular-weight compounds and very few hydrophobic drugs can pass through the skin barrier, and it is disadvantageous in that, even though passing through the skin barrier, the drug is not effective in a lesion while maintaining an appropriate amount thereof.

To address the problems of a patch, which is a first-generation transdermal drug delivery system, e.g., in terms of passing through the skin barrier and efficacy, a variety of techniques have been developed. Electroporation is a technique for applying an electric field to a cell membrane to temporarily penetrate an external substance into a cell or tissue, and is applied as a means for injecting, into cells, compounds ranging from a low-molecular-weight compound such as an anticancer agent to a high-molecular-weight compound such as DNA.

However, the electroporation system is inconvenient when used, and thus it is difficult for ordinary people to easily use this system. An ultrasound technology is a technique that non-invasively increases permeation efficiency by applying an electric field to the cell membrane through ultrasound, and is used to inject a large amount of drugs or genes into cells and tissues and is also applied as an imaging method for aid in understanding of skin tissues when injecting a drug. However, since accurate understanding of the intracellular delivery mechanism through the ultrasound technology is still lacking, much research is needed to apply the ultrasound technology as a practical transdermal drug delivery technology. A jet injection technology is a technique that does not use an injection needle and non-invasively delivers a drug in a powder or liquid form through the skin by gas pressure. Since first developed, various drugs such as vaccines, toxoids, DNA, and the like have been applied through this technology, and this technology has flexible drug applicability. However, unlike other transdermal drug delivery technologies, the jet injection technology has a problem in that a drug tends to spread widely rather than locally, and thus cannot be delivered intensively to the dermis, and shows skin side effects such as blisters, erythema, hardening, hematoma, and the like.

A microneedle is a micro-level small syringe that can overcome pain trauma infection resistance, which is a disadvantage of existing syringes, and deliver drugs and physiologically active substances with high efficiency. The microneedle is as safe as the first-generation patch, causes no pain, and can deliver an active ingredient rapidly and efficiently like injections. Biodegradable microneedles, which are one type of microneedles, load a physiologically active substance in a biodegradable polymer matrix and deliver the physiologically active substance using the mechanism of the biodegradable matrix when penetrating the skin. A variety of first-generation transdermal drug delivery systems, such as electroporation, ultrasound, jet injection, and the like, require specialist procedures, while microneedles are a self-administrative system.

Drug delivery of biodegradable microneedles is mostly based on the first-generation patch agent, in which a biodegradable microneedle structure including a drug is formed on a patch-type adhesive. For efficient drug delivery, an adhesive patch needs to be attached to the skin for about 1 hour to about 2 hours, which is the point in time when the biodegradable polymer matrix is completely dissolved, resulting in side effects such as erythema, inflammation, allergic reactions, and the like. Recent research shows that, when a biodegradable microneedle patch is applied to the skin, the microneedles do not completely penetrate into the skin, resulting in incomplete drug delivery efficiency (Ryan F. Donnelly et al. Journal of Controlled Release 147:333-341(2010)).

Examples of existing biodegradable microneedle fabrication methods include micro-molding (Jung-Hwan Park et al., Biodegradable polymer microneedles: Fabrication, mechanics and transdermal drug delivery, Journal of Controlled Release 104:51-66(2005)), drawing lithography (Kwang Lee and Hyungil Jung, Drawing lithography for microneedles: A review of fundamentals and biomedical applications, Biomaterials 33:7309-7326(2012)), droplet airborne blasting (Korean Patent Application No. 1136738), a method in which centrifugal force is used (Korean Patent Application No. 2013-0050462), and a method in which negative pressure is used (Korean Patent Application No. 2013-0019247), and all the manufacturing processes necessarily require mixing of a polymer with a drug. It is impossible to quantitatively load a drug due to the loss of a structure, occurring in a process of post-molding into a microneedle form using the polymer including a drug mixed therewith, and the amount of drug in the microneedle fabricated after molding should be subsequently evaluated. In addition, the microneedle is manufactured by a molding method using viscosity of the polymer, and thus the amount of drug that can be loaded in a patch of microneedles ranges only from several tens of micrograms to several hundreds of micrograms.

Due to mixing of a polymer with a drug during fabrication of microneedles, the polymer and the drug interact with each other, resulting in a drastic decrease in activity of the drug. The microneedle molding process necessarily requires evaporation of a solvent in the polymer, and, in this process, the structure of a drug (vaccine, hormone, antibody, and the like) of a polymer substance is modified and thus the drug cannot be used in the microneedle as a drug vehicle and, therefore, must be accompanied by a structural stabilizer such as sucrose, maltose, galactose, or the like.

To compensate for the drawbacks through polymer-drug intermixing, a technique for directly percutaneously delivering a powder-type drug was developed in the U.S.A. (Dexiang Chen et al., Nature Medicine 6:1187-190(2000)). The activity of various powdered drugs such as insulin, vaccine, and the like was tested. However, a separate device designed for high-pressure dispensing is needed to percutaneously deliver a powder-type drug, a gas should be refilled after being dispensed once, and the particle size of a sprayable powered drug is limited.

Throughout the present specification, many papers and patent documents are referred to and citations thereof are shown. The disclosures of the cited papers and patent documents are incorporated herein by reference in their entirety, and thus the level of the art to which the present invention pertains and the contents of the present invention will be explained more clearly.

SUMMARY OF THE INVENTION

The inventors of the present invention conducted extensive research and tried to address the above-described problems of the prior art. As a result, the inventors of the present invention developed a microcontainer microstructure including a microcontainer film structure having a sharp tip portion, wherein the microcontainer microstructure can be easily inserted into the human body and a drug in various states (solid-phase or liquid-phase (in particular, powder or a highly-concentrated state) can be efficiently loaded and delivered through microcontainers.

Thus, the present invention provides a microcontainer microstructure including a microcontainer film structure having a sharp tip portion.

The present invention provides a microcontainer microstructure including a microcontainer film structure having a sharp tip portion.

The sharp tip portion may be formed by applying an outward force to a separate polymer composition formed on an upper portion of the microcontainer film structure, or may be formed by additionally attaching a separate microstructure to an upper portion of the microcontainer film structure.

The microcontainer film structure may be formed in contact with an inner surface of a hole of a substrate, the hole having an upper opening and a lower opening or a closed lower end.

The microcontainer film structure may be a portion to be inserted into the human body.

The microcontainer microstructure may further include a drug loaded in microcontainers.

To seal the drug, the microcontainer microstructure may include a second film structure formed in combination with the microcontainer film structure.

The microcontainer film structure and the second film structure may be formed in an integrated form.

The microcontainer microstructure may be formed on a flat plate or a pillar.

According to an embodiment of the present invention, there is provided a microcontainer microstructure including: a substrate with a hole having an upper opening and a lower opening or a closed lower end; and a microcontainer film structure formed in contact with an inner surface of the hole and having a sharp tip portion.

According to another embodiment of the present invention, there is provided a method of manufacturing a microcontainer microstructure, the method including: (a) preparing a substrate with a hole having an upper opening and a lower opening or a closed lower end; and (b) preparing a microcontainer film structure formed in contact with an inner surface of the hole and having a sharp tip portion.

Prior to process (b), the method may further include filling the hole with a polymer composition or a thermoplastic polymer powder.

In a case in which the filling is performed using the polymer composition, in process (b) above, the preparing of the microcontainer film structure may be performed by removing a solvent of the polymer composition.

In a case in which the filling is performed using the thermoplastic polymer powder, in process (b) above, the preparing of the microcontainer film structure may be performed by plasticizing the thermoplastic polymer powder by heat and then curing the resulting thermoplastic polymer powder.

In process (b) above, the sharp tip portion may be formed by applying an outward force to a separate polymer composition formed on an upper portion of the microcontainer film structure, or may be formed by additionally binding a separate microstructure to an upper portion of the microcontainer film structure.

The method may further include (c) loading a drug in microcontainers.

The drug may be sealed by a second film structure.

The characteristics and advantages of the present invention are summarized as follows:

(a) According to the present invention, a drug loaded in microcontainers is directly used for percutaneous delivery, and thus efficacy and stability of the drug are ensured.

(b) According to the present invention, the drug loaded in microcontainers may be percutaneously delivered in a fixed or large amount.

(c) When being formed in contact with an inner surface of the hole formed in the substrate, the structure of the present invention is applied to the human body using positive pressure or physical force, and thus side effects according to existing patch products (erythema, inflammation, allergic reactions, and the like) may be overcome, and the loaded drug may be accurately delivered into the human body, and, accordingly, it is very user-friendly. In particular, when a flat plate such as a patch or the like is used, convenience of a user is enhanced, and, in the case of pillars, 100% of the loaded drug may be delivered into the human body.

DETAILED DESCRIPTION OF THE INVENTION

According to the prior art, a biodegradable microstructure is prepared by mixing a drug with a solvent and a biodegradable polymer and then using the resulting mixture, however, this may lead to a decrease in drug activity due to drug-polymer interactions and a reduction in drug activity due to drying and heating in a microstructure manufacturing process. However, the present invention is advantageous in that a powdered or highly concentrated drug may be loaded in a microstructure without mixing with a polymer, and thus these limitations may all be overcome.

The inventors of the present invention conducted extensive research and tried to address the above-described problems of the prior art. As a result, the inventors of the present invention developed a microcontainer microstructure including a microcontainer film structure having a sharp tip portion, wherein the microcontainer microstructure may be easily inserted into the human body and a drug in various states (solid-phase or liquid-phase (in particular, powder or a highly-concentrated state) can be efficiently loaded and delivered through microcontainers.

Microcontainer Microstructure (1)

The present invention provides a microcontainer microstructure including a microcontainer film structure having a sharp tip portion.

Figure 1:
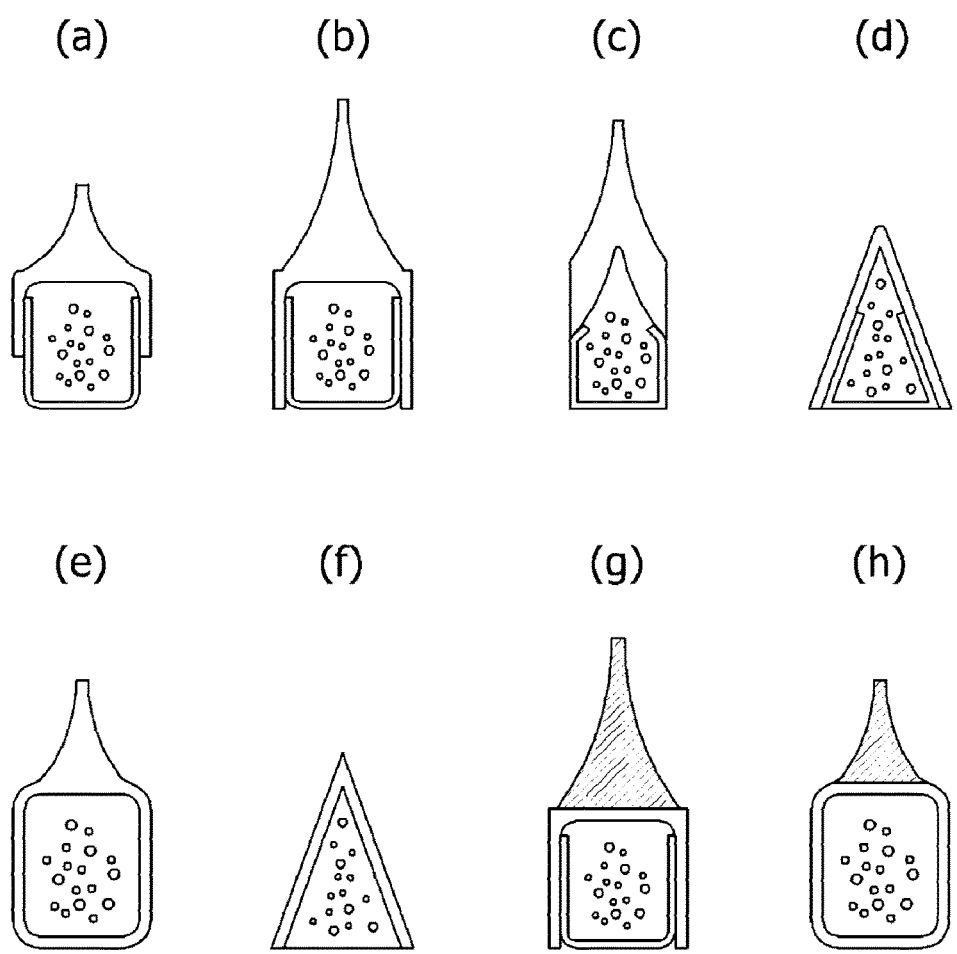
FIGS. 1 and 2 are views illustrating microcontainer microstructures according to various embodiments of the present invention.

FIG. 1 illustrates microcontainer microstructures according to various embodiments of the present invention. FIGS. 1(a) to 1(d) illustrate microcontainer microstructures each including a microcontainer film structure having a sharp tip portion, a drug loaded in microcontainers, and a second film structure. FIGS. 1(e) and 1(f) illustrate microcontainer microstructures each including a microcontainer film structure having a sharp tip portion, a drug loaded in microcontainers, and a second film structure, wherein the microcontainer film structure and the second film structure are formed in an integrated form. FIGS. 1(g) and 1(h) illustrate microcontainer microstructures each including a microcontainer film structure having a sharp tip portion, a drug loaded in microcontainers, and a second film structure, in which the sharp tip portion is formed by additionally attaching a separate microstructure to an upper portion of the microcontainer film structure.

First, a microcontainer microstructure according to the present invention includes a microcontainer film structure having a sharp tip portion.

The microcontainer film structure has a microcontainer structure. The microcontainer is a compound word of micro and room, which means an empty space in units of micrometers. For example, the microcontainer refers to a structure having a certain space with a surface area and volume in units of micrometers. For example, when microcontainers have a rectangular pillar shape, the volume of a unit microcontainer is 1,000,000,000 $\mu m^3$ or less, in particular, ranges from 100 $\mu m^3$ to 1,000,000 $\mu m^3$. Various states (solid-phase (in particular, powder) or liquid-phase) of a drug may be loaded in microcontainers.

The microcontainer film structure may be formed as a single layer or multiple layers. In addition, the microcontainer film structure may have various shapes, depths, and the like. In a case in which the microcontainer film structure has a conical tubular shape, a pyramidal tubular shape, or the like, the microcontainer film structure itself may form a sharp tip portion (see FIGS. 1(d) and 1(f)).

The microcontainer film structure may be prepared using a polymer composition or a thermoplastic polymer powder. A biocompatible or biodegradable polymer material may be used as the polymer composition or the thermoplastic polymer powder. The biocompatible material refers to a material that is substantially non-toxic to the human body, chemically inert, and non-immunogenic. In addition, the biodegradable material refers to a substance that can be decomposed by body fluid, a microorganism, or the like in vivo. When the biodegradable polymer is delivered as a drug carrier into the human body, a decomposition time thereof may be variously adjusted from several hours to several months according to the type and composition of the biodegradable polymer.

In particular, the biocompatible or biodegradable material may be hyaluronic acid or a salt thereof, polyester, polyhydroxyalkanoate (PHAs), poly($\alpha$-hydroxyacid), poly(($\beta$-hydroxyacid), poly(3-hydroxybutyrate-co-valerate) (PHBV), poly(3-hydroxyproprionate) (PHP), poly(3-hydroxyhexanoate) (PHH), poly(4-hydroxyacid), poly(4-hydroxybutyrate), poly(4-hydroxyvalerate), poly(4-hydroxyhexanoate), poly (esteramide), polycaprolactone, polylactide, polyglycolide, poly(lactide-co-glycolide) (PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazenes, PHA-PEG, ethylene vinyl alcohol copolymers (EVOH), polyurethane, silicon, polyester, polyolefin, a copolymer of polyisobutylene and ethylene alpha-olefin, a styrene-isobutylene-styrene triblock copolymer, an acrylic polymer or copolymer, a vinyl halide polymer or copolymer, polyvinyl chloride, polyvinyl ether, polyvinyl methyl ether, polyvinylidene halides, polyvinylidene fluoride, polyvinylidene chloride, polyfluoroalkenes, polyperfluoroalkenes, polyacrylonitrile, polyvinyl ketone, polyvinyl aromatics, polystyrene, polyvinyl ester, polyvinyl acetate, an ethylene-methyl methacrylate copolymer, an acrylonitrile-styrene copolymer, a copolymer of ABS resin and ethylene-vinyl acetate, polyamides, alkyd resins, polyoxymethylene, polyimides, polyethers, polyacrylate, polymethacrylate, polyacrylic acid-co-maleic acid, chitosan, dextran, cellulose, cellulose polymers (e.g., hydroxypropyl methylcellulose, hydroxyalkyl cellulose, hydroxyethyl cellulose, hydroxypropyl cellulose, ethyl hydroxyethyl cellulose, alkyl cellulose, and carboxymethylcellulose), heparin, alginate, inulin, starch, or glycogen, but the present invention is not limited thereto.

In particular, in the present invention, hyaluronic acid or carboxymethylcellulose is used as the polymer composition, and poly(lactide-co-glycolide) (PLGA) is used as the thermoplastic polymer powder.

The microcontainer film structure may be prepared by additionally mixing the polymer composition or the thermoplastic polymer powder with a separate drug. That is, the microcontainer microstructure may also include, in addition to the drug loaded in microcontainers, a separate drug that is identical to or different from the drug loaded in microcontainers. The type of the separate drug is the same as described below in description of the drug loaded in microcontainers.

The microcontainer film structure may be a portion to be inserted into the human body, and has a sharp tip portion insertable into the human body, and the microcontainer film structure itself may have a sharp tip portion (see FIG. 2(c)). The sharp tip portion may be formed by applying an outward force to a separate polymer composition formed on an upper portion of the microcontainer film structure, or may be formed by additionally attaching a separate microstructure to an upper portion of the microcontainer film structure.

In this regard, the human body refers to all of a human body that can be exposed to the outside, including the skin, paranasal cavities, esophagus, respiratory tract, urethra, bile duct, and the like.

The microcontainer film structure itself may have a sharp tip portion, and the sharp tip portion may be formed by micro-molding, and formed by applying an outward force to a polymer composition for preparation of the microcontainer film structure.

In particular, in a case in which the sharp tip portion is formed by applying an outward force to a polymer composition for preparation of the microcontainer film structure, the sharp tip portion may be formed according to the following methods.

Figure 9A:
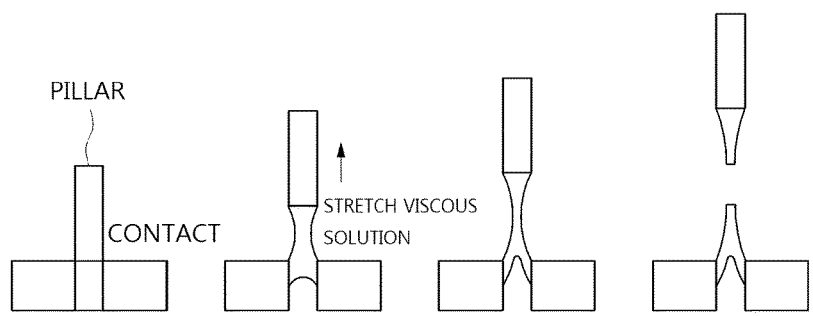
FIGS. 9(a) to 9(h) are views and images illustrating preparation of microcontainer film structures having a sharp tip portion, according to various embodiments of the present invention.

The first method is a method described in Korean Patent Application No. 0793615, developed by the inventors of the present invention. The first method is performed by bringing the polymer composition filled in the hole in contact with a pillar of a substrate and then relatively moving the pillar with respect to the substrate (see FIG. 9(a)). Relative movement of the pillar with respect to the substrate may be performed by, for example, vertically moving the pillar with respect to the substrate or vertically moving the substrate with respect to the pillar. In the relative movement process, a polymer composition at a top end of the pillar is stretched and the polymer composition is cured during the stretching process, thereby completing the fabrication of a microstructure.

Figure 9B:
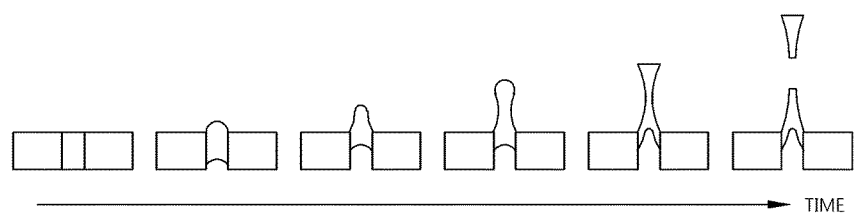

The second method is a method described in Korean Patent Application No. 2013-0050462, developed by the inventors of the present invention (centrifugal force method). A microstructure is formed by applying centrifugal force to the polymer composition filled in the holes (see FIG. 9(b)).

Figure 9C:
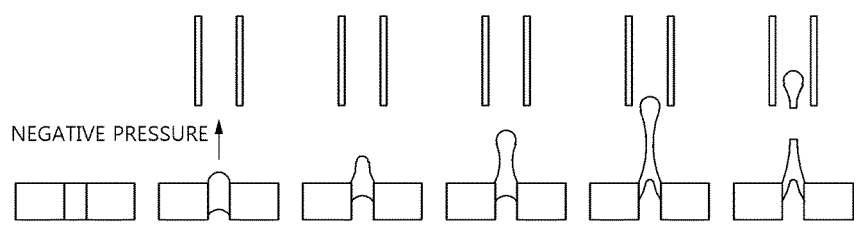

The third method is a method described in Korean Patent Application Registration No. 10-1488397, developed by the inventors of the present invention (Negative pressure method). A microstructure is formed by applying negative pressure to the polymer composition filled in the holes (see FIG. 9(c)).

The fourth method is a method described in Korean Patent Application No. 2015-0072107, developed by the inventors of the present invention (Preparation of microstructure by CCDP). A microstructure is formed by dispensing a polymer composition onto the microcontainer film structure and stretching the resulting structure.

The fifth method is a method disclosed in Korean Patent Application No. 10-1136738, developed by the inventors of the present invention (Preparation of solid microstructure by air blowing). A microstructure is formed by dispensing a polymer composition onto the microcontainer film structure, stretching the resulting structure, and blowing air thereto.

The aforementioned technologies are embodiments of a method of forming a sharp tip portion for inserting the microcontainer film structure into the human body, made by the inventors of the present invention.

Meanwhile, the polymer composition may be formed as multiple layers to fill the holes formed in the substrate. For example, the holes may be filled with multiple layers of different types of polymer compositions, a polymer composition and a drug, or different types of a polymer composition and a drug.

Figure 9D:
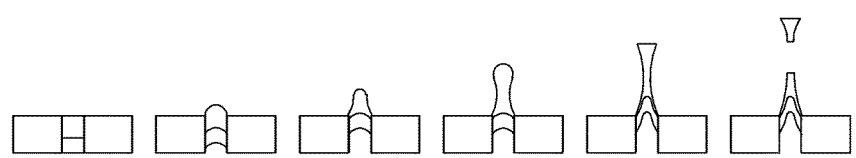
Figure 9E:
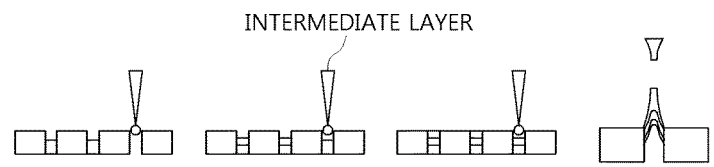

For example, a microcontainer film structure having a two-layered sharp tip portion may be obtained by filling the holes with two layers of the polymer composition (see FIG. 9(d). A microcontainer film structure having a three-layered sharp tip portion may be obtained by filling the holes with three layers of the polymer composition (see FIG. 9(e)). As described above, in a case in which the sharp tip portion is formed by applying an outward force to the polymer composition, the sharp tip portion may also function as a film structure.

Figure 9F:
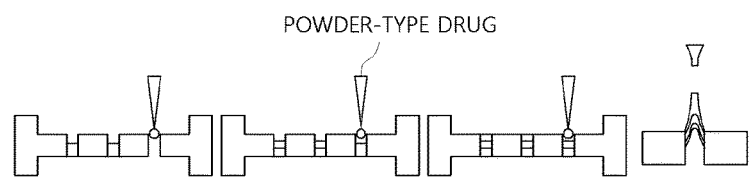

In the microcontainer film structure having a layered sharp tip portion, layers of different types of polymer compositions are formed, whereby a decomposition time thereof according to each layer may be variously adjusted from several hours to several months when delivered as a drug carrier into the human body. In particular, in the case of forming the sharp tip portion as three layers, a biodegradable polymer is positioned in upper and lower layers, and a powder-type drug is positioned in an intermediate layer, followed by molding, thereby preparing a microcontainer film structure with a powder-type drug loaded in the intermediate layer thereof (see FIG. 9(f)).

Figure 9G:
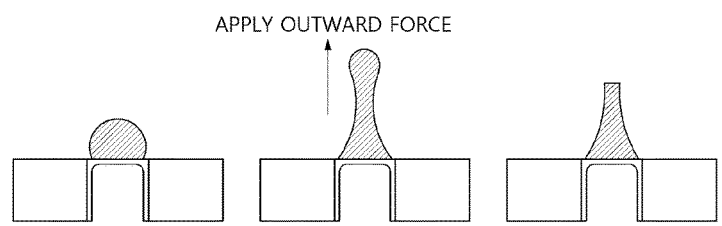

The sharp tip portion may also be formed by applying an outward force to a separate polymer composition formed on an upper portion of the microcontainer film structure (see FIG. 9(g)).

The separate polymer composition for forming the sharp tip portion may be identical to or different from the polymer composition used in the microcontainer film structure.

The separate polymer composition may be a viscous composition, and the viscous composition refers to a composition capable of being deformed by a force applied to the viscous composition so as to form a sharp tip portion.

The viscosity of such a viscous composition may be variously varied by intrinsic viscosity depending on the type, concentration, temperature and mixing ratio of polymer compositions, or may be appropriately adjusted according to the purpose of the present invention by adding a viscosity modifying agent to the composition.

For example, the viscosity of the viscous composition may be appropriately adjusted according to the purpose of the present invention by adding, to the composition including a main component of the sharp tip portion, e.g., a biocompatible and/or biodegradable material, a viscosity modifying agent commonly used in the art, for example, hyaluronic acid or a salt thereof, polyvinyl pyrrolidone, a cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, gum Arabic, alginic acid, gelatin, gellan gum, carrageenan, karaya gum, curdlan, chitosan, chitin, tara gum, tamarind gum, fragacanth gum, furcelleran, pectin, or pullulan. According to one embodiment of the present invention, the viscous composition used in the present invention has a viscosity of 200,000 cSt or less.

The viscous composition is dissolved in a suitable solvent, thereby exhibiting viscosity. Meanwhile, viscous substances may exhibit viscosity when melted by heat. To maximize the advantage of a non-heating process, materials used in the viscous composition exhibit viscosity when dissolved in a suitable solvent. The solvent used to dissolve a viscous material for preparation of a viscous composition is not particularly limited, and may be water, an anhydrous or hydrous lower alcohol having 1 to 4 carbon atoms, acetone, ethyl acetate, chloroform, 1,3-butylene glycol, hexane, diethyl ether, or butyl acetate.

The sharp tip portion may have various shapes, for example, may be in the form of a microneedle, a microblade, a microknife, a microfiber, a microspike, a microprobe, a microbarb, a microarray, or a microelectrode.

The sharp tip portion may have various dimensions. For example, a top end of the sharp tip portion has a diameter of 1 µm to 500 µm, 2 µm to 300 µm, or 5 µm to 100 µm, and the sharp tip portion has an effective length of 100 µm to 10,000 µm, 200 µm to 10,000 µm, 300 µm to 8,000 µm, or 500 µm to 2,000 µm. The top end of the sharp tip portion refers to one end of the sharp tip portion having a minimum diameter, the effective length refers to a vertical length from the top end of the sharp tip portion to the surface of a support, and a lower end of the sharp tip portion refers to one end of the sharp tip portion having a maximum diameter. For example, in the present invention, the lower end of the sharp tip portion has a diameter of 50 µm to 1,000 µm, and the sharp tip portion has an effective length of 100 µm to 10,000 µm, 200 µm to 10,000 µm, 300 µm to 8,000 µm, or 500 µm to 2,000 µm.

The formation of the sharp tip portion may be variously performed by various methods known in the art and the methods developed by the inventors of the present invention.

The microcontainer film structure may be prepared by, in addition to micromolding, various known methods used for preparation of oral capsules, such as a pillar dipping method, and the like.

When the micro-molding method is used, the microcontainer film structure may be formed in contact with an inner surface of each hole of the substrate, having an upper opening and a lower opening or a closed lower end. A detailed description of the micro-molding method will be provided in microcontainer microstructure (2) below.

Figure 8A:
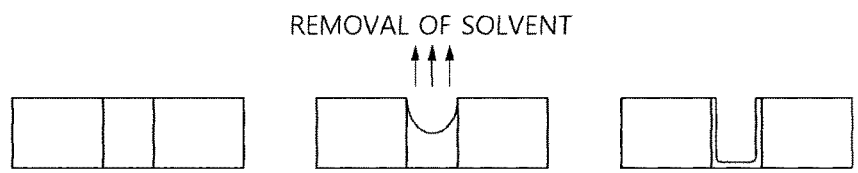
FIGS. 8(a) to 8(h) are views and images illustrating preparation of microcontainer film structures according to various embodiments of the present invention.
Figure 8B:
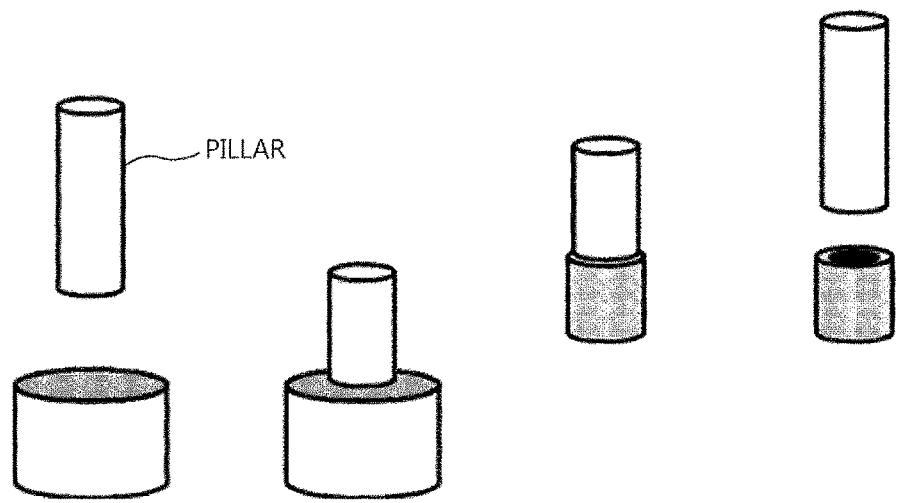

When the pillar dipping method is used, a micro-sized pillar may be dipped into a polymer composition, followed by drying and separation of the resulting structure from the pillar, thereby completing the preparation of a microcontainer film structure (see FIG. 8(b)). The thickness of the film structure may be adjusted by repeating the dipping and drying processes, and thus a decomposition rate thereof may be adjusted when inserted by physical force into the human body.

Next, the microcontainer microstructure according to the present invention may include the drug loaded in microcontainers.

The drug refers to a broad concept, and includes energy, nano components, cosmetic ingredients (e.g., wrinkle improving agents, skin aging inhibitors, and skin lightening agents), cell culture fluids, and the like, as well as therapeutic agents for therapeutic purposes after consultation.

In particular, the therapeutic agents include chemical drugs, protein/peptide drugs, peptide drugs, nucleic acid molecules for genetic treatment, and the like.

For example, non-limiting examples of the therapeutic agents include an anti-inflammatory agent, a painkiller, an anti-arthritic agent, an antispasmodic agent, an antidepressant agent, an antipsychotic agent, a tranquilizer, an antianxiety drug, a narcotic antagonist, an antiparkinson's disease drug, a cholinergic agonist, an anticancer agent, an antiangiogenic inhibitor, an immunosuppressant, an antiviral agent, an antibiotic, an anorectic agent, an anticholinergic drug, an antihistaminic agent, an antimigraine agent, a hormonal agent, a coronary vessel, a cerebrovascular or peripheral vasodilator, a contraceptive, an antithrombotic, a diuretic, an antihypertensive, and a therapeutic agent for cardiovascular disorders.

In particular, non-limiting examples of the protein/peptide drug include a hormone, a hormone analogue, an enzyme, an enzyme inhibitor, a signal transduction protein or a fragment thereof, an antibody or a fragment thereof, a single chain antibody, a binding protein or a binding domain thereof, an antigen, an adhesive protein, a structural protein, a regulatory protein, a toxin protein, a cytokine, a transcription factor, a blood coagulation factor, and a vaccine. More particularly, the protein/peptide drug may include insulin, insulin-like growth factor 1 (IGF-1), growth hormones, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypres sin, octreotide, oxytocin, pitressin, secretin, sincalide, terlipres sin, thymopentin, thymosine α1, triptorelin, bivalirudin, carbetocin, cyclosporine, exedine, lanreotide, luteinizing hormone-releasing hormone (LHRH), nafarelin, parathyroid hormone, pramlintide, enfuvirtide (T-20), thymalfasin, and ziconotide.

The energy may include thermal energy, light energy, electrical energy, and the like. For example, in photodynamic therapy, the microcontainer microstructure may be used to induce light to a specific site inside the body so as to allow light to directly act on the tissue or allow light to act on a mediator such as light-sensitive molecules.

The drug may be in various states, and may be in a solid phase or liquid phase, in particular, in a powder or highly concentrated form.

Figure 10A:
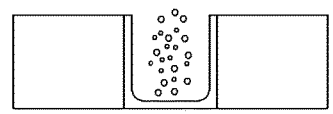
FIGS. 10(a) to 10(g) are views and images illustrating loading of a drug in microcontainers, according to various embodiments of the present invention.

When the drug is in a solid phase, in particular, in a powder form, loading (filling) of the drug in microcontainers may be performed using various methods (see FIG. 10(a)), and may be performed using the same method as that used for filling the holes of the substrate with the powdered drug.

When the drug is in a liquid phase, in particular, in a highly concentrated state, loading of the drug in microcontainers may be performed using the same method as that used for filling the holes of the substrate with the polymer composition, in particular, using a physical method using centrifugal force and vacuum, a chemical method, and a method in which an electromagnetic force is used. For example, the liquid-phase drug may be loaded through droplet dispensing thereof into empty spaces of microcontainers, and filling thereof may be performed by centrifugal force or vacuum.

Figure 10B:
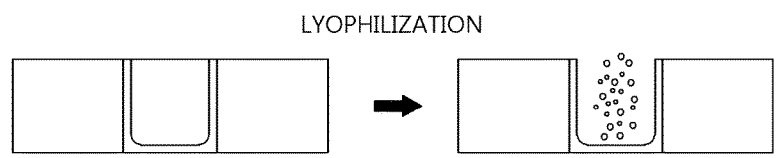

Alternatively, microcontainers may be filled with a liquid-phase protein/peptide drug, followed by lyophilization, and the resulting protein/peptide drug may be converted into a powder form. In particular, the microcontainers may be filled with a liquid-phase drug, followed by in situ lyophilization together with a film, thereby obtaining a powder-type sample-filled film structure (see FIG. 10(b)).

When the drug used in the present invention is a drug susceptible to heat, such as a protein drug, a peptide drug, vitamins (particularly, vitamin C), nucleic acid molecules for genetic treatment, and the like, the microcontainer microstructure may be manufactured under non-heating treatment conditions, at room temperature, or at low temperatures lower than room temperature (e.g., in the range of 5☐ to 20☐).

Meanwhile, a space except for a space of the microcontainers with the drug loaded therein may be filled with a gas or a polymer composition. Examples of the polymer composition have already been provided above.

Next, the microcontainer microstructure according to the present invention may include a second film structure formed in combination with the microcontainer film structure, to seal the drug.

Figure 10C:
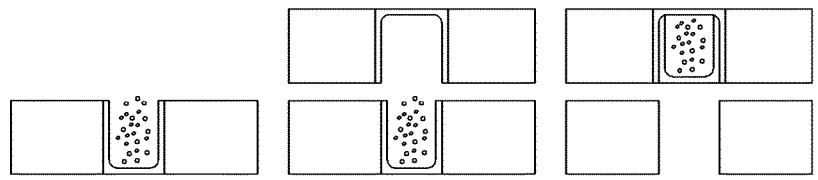

Upper and lower ends of the second film structure and the microcontainer film structure may be combined, thereby sealing the drug (see FIG. 10(c)). Referring to FIG. 10(c), the drug may be loaded in the microcontainer film structure, and then the microcontainer film structure and the second film structure are aligned with respect to each other, followed by separation of the resulting structure from the substrate with holes formed therein, thereby completing the preparation of a film structure in which the upper and lower ends of the respective structures are combined with each other. To more suitably seal the drug, the microcontainer film structure and the second film structure may be formed in an integrated form.

The second film structure may be prepared using a polymer composition or a thermoplastic polymer powder as in the microcontainer film structure, and examples of suitable polymer compositions or thermoplastic polymer powders have already been provided above.

The microcontainer microstructure according to the present invention may be formed in contact with an inner surface of each hole formed in the substrate, or may be formed on a flat plate such as a patch or the like, or a pillar. In particular, when a flat plate such as a patch or the like is used, convenience of a user is enhanced, and, when not applied to a patch, side effects according to existing patch products (erythema, inflammation, allergic reactions, and the like) may be overcome, and the loaded drug may be accurately delivered into the human body, resulting in very high user convenience. In particular, in the case of pillars, 100% of the loaded drug may be delivered into the human body.

In addition, according to the microcontainer microstructure of the present invention, various forces such as a physical force using a pillar structure, an indirect force using positive pressure, a chemical force using a chemical reaction, and/or an electrical force directly act on the microcontainer microstructure to separate the microcontainer film structure from the substrate to be inserted into the human body. The forces used for separation therebetween may be used alone or in combination. Various forces may be designed as an actuator and act alone or in combination.

Figure 11A:
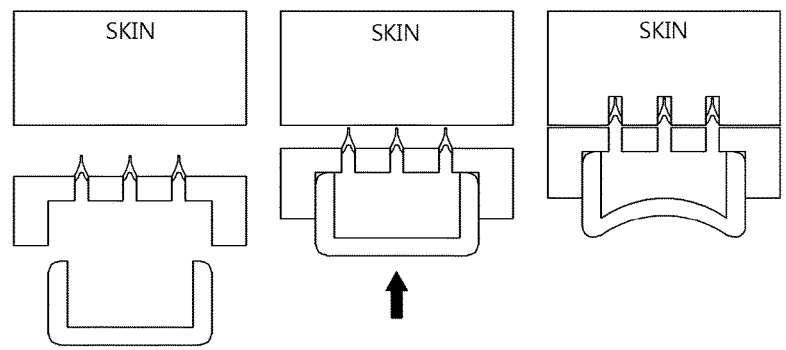
FIGS. 11(a) to 11(d) are views illustrating insertion of microcontainer microstructures according to various embodiments of the present invention into the human body.
Figure 11B:
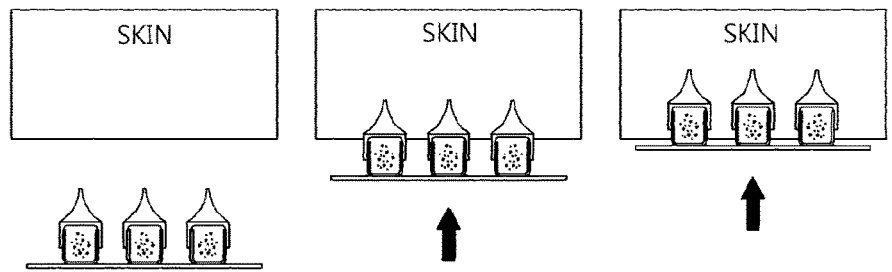
Figure 11C:
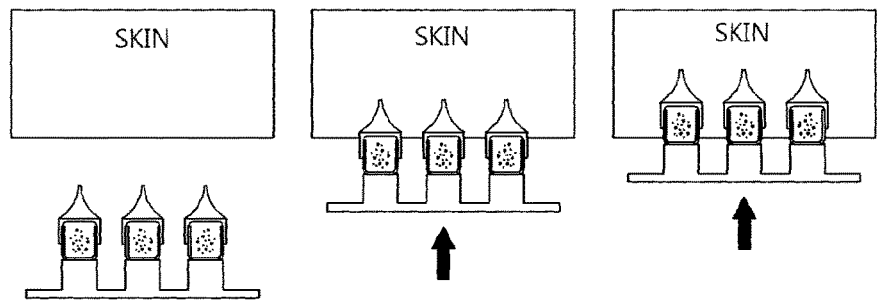

FIGS. 11(a) to 11(c) illustrate the manner by which the microcontainer film structures are inserted into the human body using positive pressure. A lower end portion of the microcontainer film structure is positioned on an inner side surface of the hole, a flat plate, and a pillar, and thus may be easily separated from the substrate, the flat plate, or the pillar using positive pressure by a finger of a human and inserted into the human body.

Figure 11D:
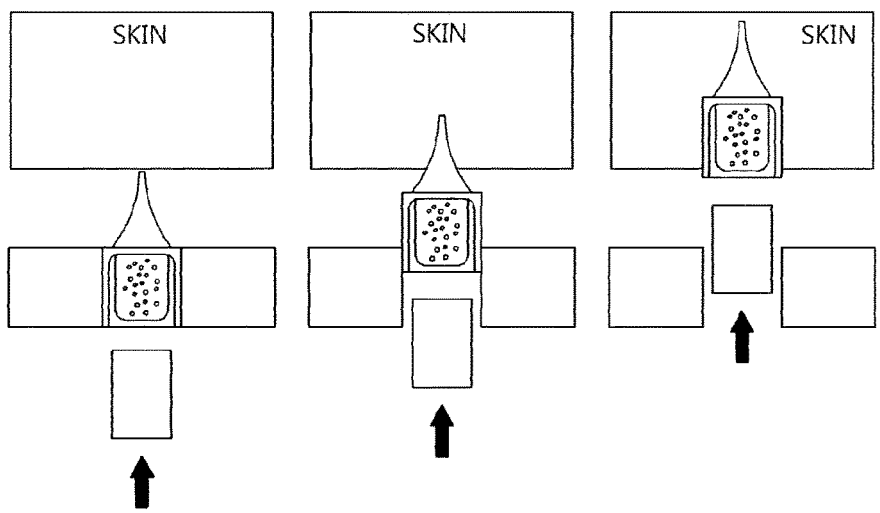

FIG. 11(d) illustrates the manner by which a capsule structure in a microcontainer is inserted into the human body using the physical force of a pillar structure.

The microcontainer microstructure is expressed in units of micrometers throughout the present specification, but the scope of the present invention is not limited to only the micro-level. However, when applied to the human body, a micro-sized structure has a pain relief effect on patients.

To insert the microstructure into the human body, it is commonly known in the art that the microstructure may have a fracture force of 0.058 N (M. Kim et al., Int J Cosmet Sci. 36(3):207-12(2014)). To be inserted into the human body, the microcontainer microstructure may be manufactured to have a fracture force of 0.058 N or more by adjusting the above-described factors, such as the type, molecular weight, and concentration of a polymer composition, and the number of coatings thereof, in the manufacturing process, but the present invention is not particularly limited to the fracture force of 0.058 N or more in the manufacturing process.

Microcontainer Microstructure (2) and Method of Manufacturing the Same

The present invention provides a microcontainer microstructure including: a substrate provided with holes having an upper opening and a lower opening or a closed lower end; and a microcontainer film structure formed in contact with an inner surface of each hole and having a sharp tip portion.

Figure 2:
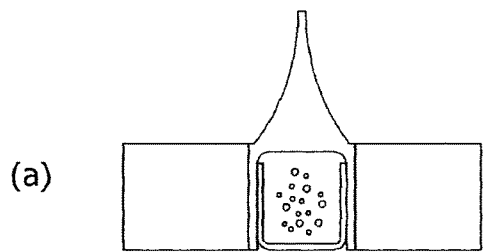
Figure 2:
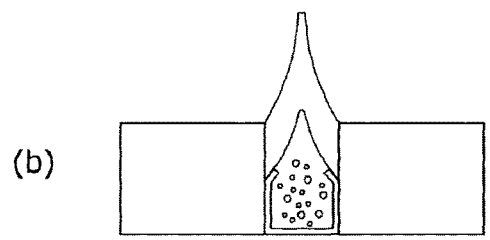
Figure 2:
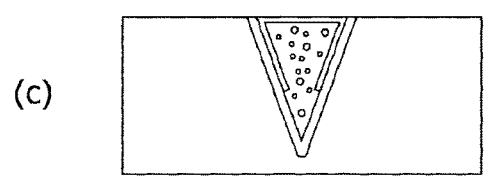
Figure 2:
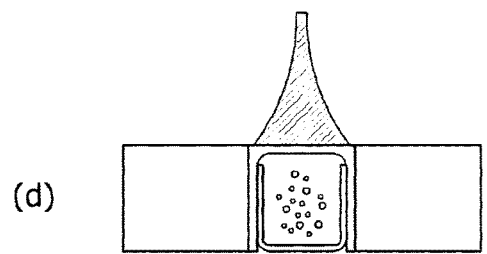

FIG. 2 illustrates microcontainer microstructures according to various embodiments of the present invention. FIGS. 2(a) to 2(c) are views of microcontainer microstructures each including: a microcontainer film structure formed in contact with an inner surface of a hole formed in a substrate and having a sharp tip portion; a drug; and a second film structure. FIG. 2(d) is a view of a microcontainer microstructure including a microcontainer film structure formed in contact with an inner surface of a hole formed in a substrate and having a sharp tip portion; a drug; and a second film structure, in which the sharp tip portion is formed by additionally attaching a separate microstructure to an upper portion of the microcontainer film structure.

The present invention also provides a method of manufacturing a microcontainer microstructure, the method including: (a) preparing a substrate provided with holes having an upper opening and a lower opening or a closed lower end; and (b) preparing a microcontainer film structure formed in contact with an inner surface of each hole and having a sharp tip portion.

Figure 3:
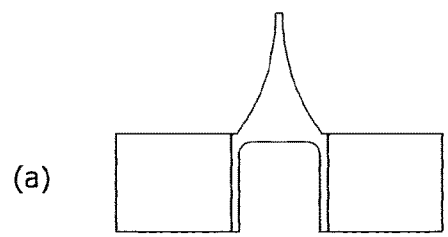
FIG. 3 illustrates microcontainer film structures having a sharp tip portion, according to various embodiments of the present invention.
Figure 3:
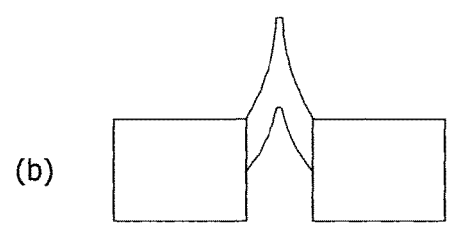
Figure 3:
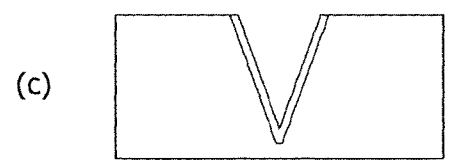
Figure 3:
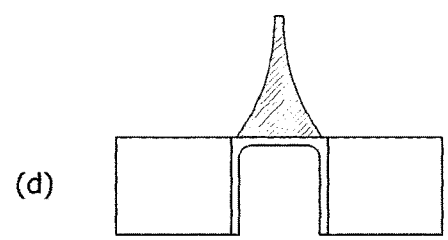
Figure 4:
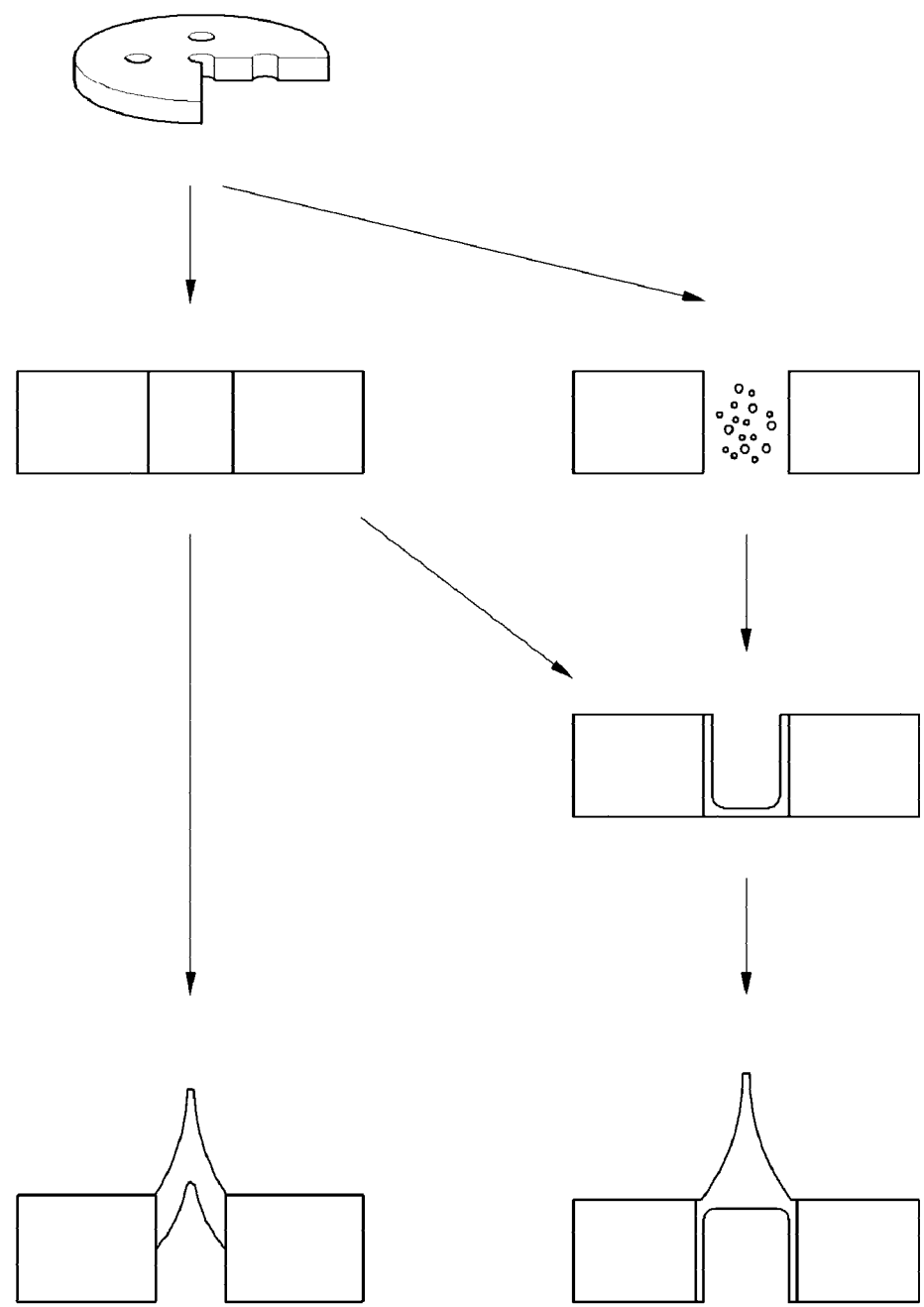
FIG. 4 illustrates a process of preparing the microcontainer film structures having a sharp tip portion, according to various embodiments of the present invention.

FIGS. 3 and 4 illustrate microcontainer film structures each having a sharp tip portion and preparation of the microcontainer film structures, according to various embodiments of the present invention. Referring to FIGS. 3 and 4, the microcontainer film structure may be prepared using a micro-molding method.

First, to prepare the microcontainer film structure, a substrate provided with a hole having an upper opening and a lower opening or a closed lower end is prepared (process (a)).

The substrate is provided with a hole having an upper opening and a lower opening or a closed lower end. The microcontainer film structure is prepared from the substrate, and thus the surface area and volume of a microcontainer space prepared from the microcontainer film structure are similar to those of the hole formed in the substrate.

Thus, the substrate has any shape having a space that allows a hole to be formed therein or includes any material that allows holes to be formed therein. The material used for preparation of the substrate includes various metals, ceramics, polymers, and composite materials, and, in particular, includes silicon derivatives such as polysiloxane (e.g., polydimethylsiloxane (PDMS)), or thermoplastic polymers, such as polystyrene, polyethylene, poly(methyl methacrylate) (PMMA), acrylonitrile butadiene styrene (ABS), polyamides, polybenzimidazole, polypropylene, polyvinyl chloride, polylactide (PLA), polyglycolide (PGA), poly lactic-co-glycolic acid (PLGA), polyvinylpyrrolidine (PVP), polyhydroxyalkanoates (PHA), or a copolymer thereof (e.g., a PDMS-PMMA copolymer).

The substrate may be prepared using various methods.

According to the first method, a material for forming the substrate, for example, a thermoplastic polymer composition, may be heated to be converted into a glassy state, and then a pillar structure (e.g., a cylindrical structure or a rectangular pillar shape) may be inserted thereinto, followed by solidification, thereby obtaining a substrate with a hole formed therein.

Figure 5B:
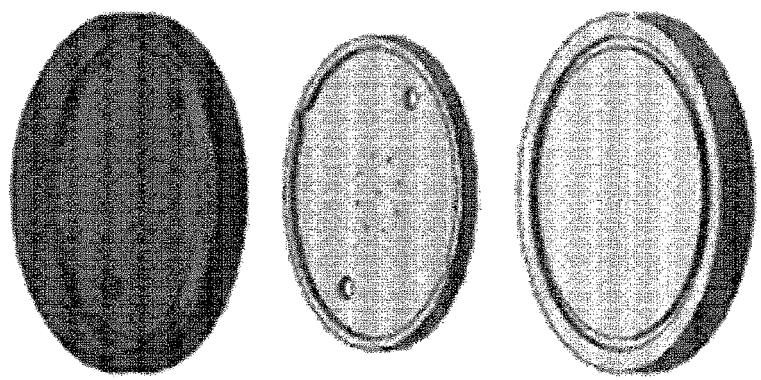
FIGS. 5(*a*) and 5(*b*) illustrate mold templates for a substrate provided with holes, according to various embodiments of the present invention, and FIGS. 5(*c*) to 5(*e*) illustrate a diagram and images of substrates each provided with holes, according to various embodiments of the present invention.

The second method is performed according to molding. In this method, a material for forming the substrate, e.g., a thermoplastic polymer composition, is added to a template with a pillar structure (e.g., a cylindrical structure or a rectangular pillar shape) formed on a surface thereof (see FIG. 5(a)) and solidified, and then the solidified resultant is separated from the template, thereby obtaining a substrate with holes formed therein. The template may be fabricated using various substances, e.g., a metal, silicon, glass, and the like. The template may be made of various metallic materials by laser cutting technology. The template may be fabricated to various shapes such as circular, tetragonal, and polygonal shapes, and a substrate with holes formed therein, prepared using the template, may have various shapes, such as circular, tetragonal, and polygonal shapes, which are shapes of the template, according to the molding method. The template may be formed as a single plate or may include upper and lower plates (see FIG. 5(b)). For example, the template may include an upper plate with a pillar structure formed on a surface thereof and a lower plate to accommodate the thermoplastic polymer composition. The thermoplastic polymer composition may be added to the lower plate, and then the lower plate may be covered by the upper plate, followed by solidification thereof for a certain period of time and separation of the solidified resultant from the upper or lower plate, thereby obtaining a substrate with holes formed therein.

In addition, in the case of using a polymer material, a substrate with holes formed therein may be prepared using various soft fabrication technologies commonly used in the art, such as hot embossing, microtransfer molding, injection molding, or the like. In the case of using a metallic material or a ceramic material, a substrate with holes formed therein may be prepared through various processing methods. Thus, the present invention is not limited to the aforementioned manufacturing methods, and, ultimately, it is significant that a hole-formed substrate structure, capable of forming microcontainers, which are empty spaces, using the film structure, is formed.

Figure 5A:
Figure 5C:
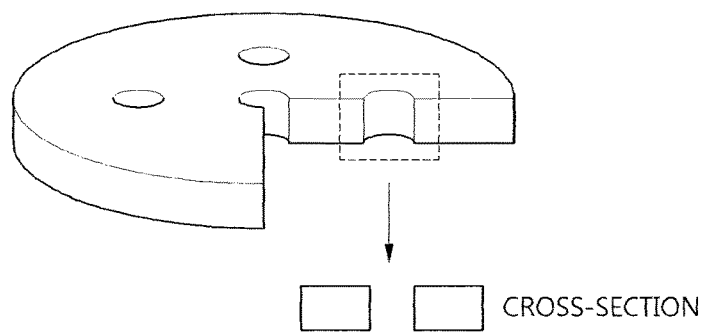

The substrate with holes formed therein, manufactured using the above-described process, may have a shape as illustrated in FIG. 5(c). Referring to FIG. 5(c), the hole has upper and lower openings. According to need, a hole having an upper opening and a closed lower end may be formed.

Next, a microcontainer film structure formed in contact with inner surfaces of the holes and having a sharp tip portion is prepared (process (b)).

The microcontainer film structure may be prepared according to, largely, two methods as follows.

According to the first method, when the holes are filled with a polymer composition, the microcontainer film structure is prepared by removing a solvent of the polymer composition.

When the solvent of the polymer composition filled in the substrate with holes formed therein is removed by drying, a thin film structure may be formed in the inner surfaces of the holes (see FIG. 8(a)). The thickness of the film, the physical strength of the film, and a decomposition rate when the film structure is inserted into the human body may be adjusted depending on the type, molecular weight, and/or concentration of the polymer composition. In addition, by repeating the filling and drying processes of the polymer composition, the thickness of the film structure, the physical strength thereof, and the decomposition rate when the film structure is inserted into the human body may be adjusted.

Figure 6:
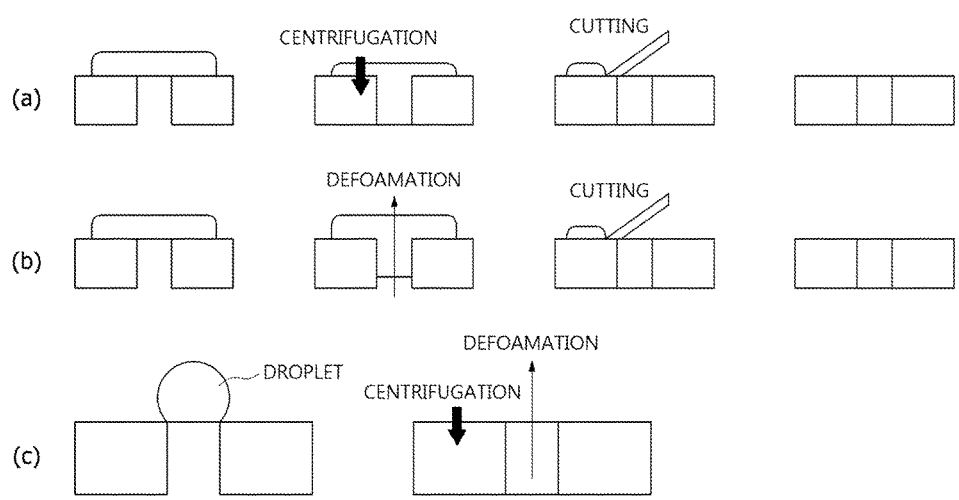
FIG. 6 illustrates views for a process of filling holes with a polymer composition, according to various embodiments of the present invention.

The holes may be filled with the polymer composition using various methods, e.g., a physical method such as centrifugal force and vacuum, a chemical method, and a method in which electrical force is used. As an example of using centrifugal force, a substrate is coated with a biodegradable polymer composition and then filled therewith using a centrifuge, followed by cutting to remove the remaining polymer composition (see FIG. 6(a)). As an example of using vacuum, holes and the periphery thereof are coated with a biodegradable polymer composition and then filled therewith by defoamation of a vacuum chamber, followed by a cutting process to remove the remaining polymer composition (see FIG. 6(b)). As another example, to omit the above-described cutting process, the biodegradable polymer composition may be droplet-dispensed to the substrate, instead of coating of the substrate therewith, and then the filling process may be performed by applying centrifugal force or vacuum to the resulting structure (see FIG. 6(c)). The biodegradable polymer composition may be dispensed dropwise onto a space of the substrate, in which microcontainers are to be formed, to prevent the biodegradable polymer composition from being coated on a surface of the substrate except for the space. In another embodiment, a dispensing nozzle having an outer diameter that is smaller than the size of a space of the substrate where a microcontainer is to be formed may be used to perform a direct filling process.

Figure 8C:
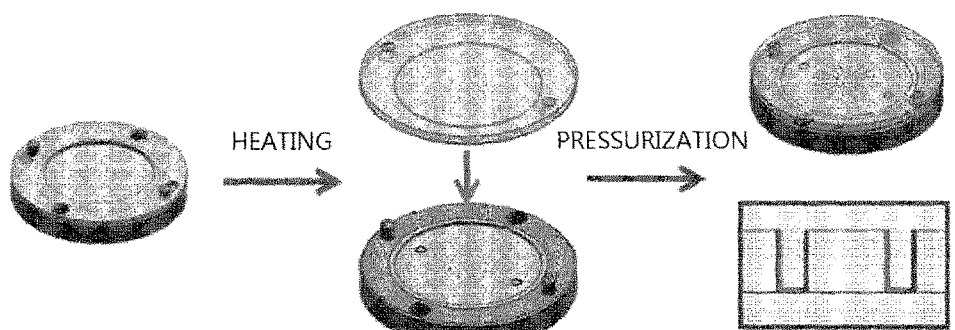

According to the second method, when the substrate with holes formed therein is filled with a thermoplastic polymer powder, the thermoplastic polymer powder is heated to be converted into a glassy state, and then the glassy resultant is pressurized and cooled down to form a film structure. In the heating process, when reaching a glass transition temperature, the thermoplastic polymer powder is converted into a glassy state, and the pressurizing process may be performed by pressing the glassy resultant with a pillar structure having a smaller diameter than that of the substrate with holes formed therein (see FIG. 8(c)).

The process of filling the holes with the thermoplastic polymer powder may be performed using various methods as follows.

Figure 7A:
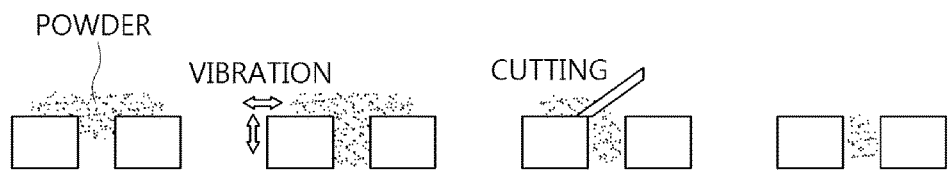
FIGS. 7(a) to 7(g) are views and images illustrating a process of filling holes with powder (a thermoplastic polymer powder or a drug powder), according to various embodiments of the present invention.

According to the first method, holes are filled with a powder using an oscillator. The holes are coated with the powder-type sample, and then microcontainers are filled with the powder-type sample using an oscillator. After the filling process, the remaining powder-type sample is removed through a cutting process, thereby completing the process of filling the holes with the powder-type sample (see FIG. 7(a)). To omit the cutting process, a powder guide is seated in the holes and the holes are filled therewith, and then the remaining powder is removed by rotating a guide, thereby preventing the powder-type sample from being coated on a surface of the substrate except for the holes (see FIG. 7(g)).

According to the second method, holes are filled with a powder using an injector. The powder-type sample is quantitatively measured, and then the holes are filled therewith using a funnel-shaped injector (see FIG. 7(d)). Each hole may be filled with the powder-type sample using an injector or an array of a plurality of holes may be simultaneously filled with the powder-type sample.

According to the third method, holes are filled with a powder using a dispenser. The holes may be filled with the powder-type sample using a dispenser having a tip through which the powder can be dispensed into the holes. To fill an array of holes formed in the substrate with a powder, the tip portion moves in X-axis, Y-axis and Z axis directions to correspond to the array of holes, thereby filling the holes with the powder (see FIG. 7(e)). In another embodiment, the array of holes may be simultaneously filled with the powder-type sample using an array of tips aligned to correspond to the array of holes (see FIG. 7(f)).

The microcontainer film structure may itself have a sharp tip portion, or the sharp tip portion may be formed by applying an outward force to a separate polymer composition formed on an upper portion of the microcontainer film structure, or may be formed by additionally binding a separate microstructure to an upper portion of the microcontainer film structure. A detailed description of the method of forming a sharp tip portion has already been provided above.

Next, the method may further include loading a drug in the microcontainers, and the drug may be sealed by a second film structure (process (c)). A detailed description of the drug and the second film structure has already been provided above.

Hereinafter, the present invention will be described in further detail with reference to the following examples. It will be obvious to one of ordinary skill in the art that these examples are provided only for illustrative purposes, and are not intended to limit the scope of the present invention according to the essence of the present invention.

EXAMPLES

Example 1

Fabrication of Template for Substrate with Holes Formed Therein

A template for a substrate with holes formed therein was fabricated using a molding method according to a micro electro mechanical systems (MEMS) process.

First, to fabricate the template for a substrate with holes formed therein, a circular template formed of steel use stainless (SUS) was fabricated using a laser cutting technology, and pillars having a diameter of 190 µm and a length of 770 µm were formed on a surface of the template (see FIG. 5(a)).

Figure 5D:
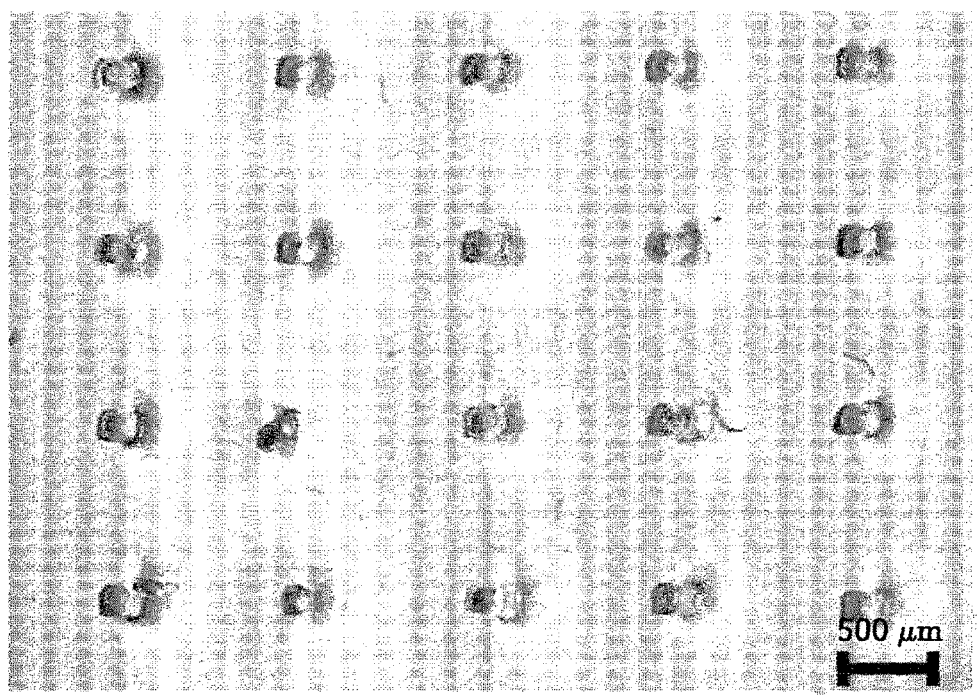
Figure 5E:
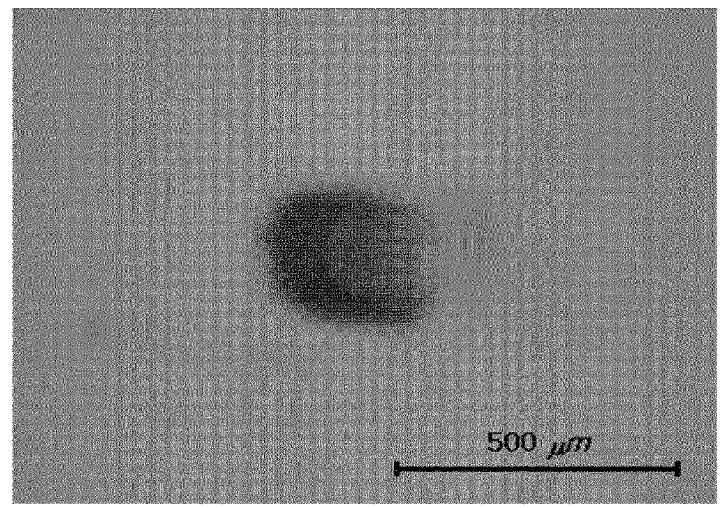

Subsequently, a polydimethylsiloxane (PDMS) solution was poured into the template and solidified, thereby completing the fabrication of a substrate with holes formed therein (see FIGS. 5(d) and 5(e)). FIG. 5(d) illustrates a cylindrical PDMS substrate with holes formed therein, and FIG. 5(e) illustrates a rectangular pillar-shaped PDMS substrate with holes formed therein.

Example 2

Filling Substrate with Holes Formed Therein with Powder-type Sample

A substrate with cylindrical holes formed therein, formed of solidified PDMS, was coated with a powder-type calcein (fluorescent dye, Sigma-Aldrich) sample, vibrated, and then subjected to a cutting process, thereby completing the process of filling the holes with the sample.

The powder-type calcein sample was coated on surfaces of the holes, and then the vibrating process was performed using a vortex (Vortex-genie, Scientific Industries), and the cutting process was performed by cutting the surface of the film structure using an edge blade (DORCO).

Figure 7B:
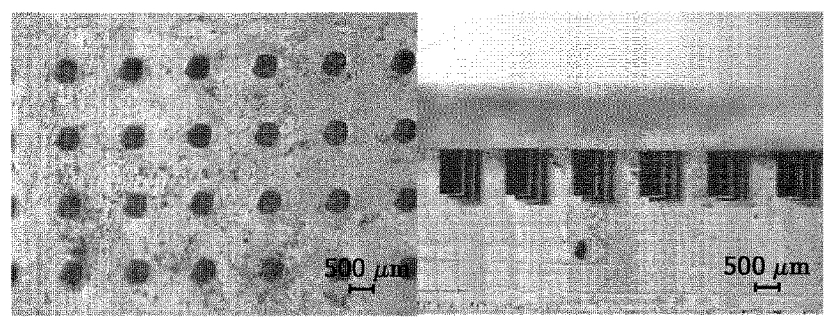
Figure 7C:
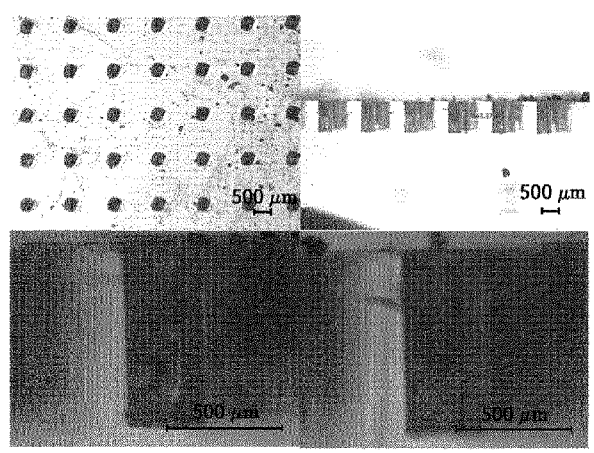
Figure 7D:
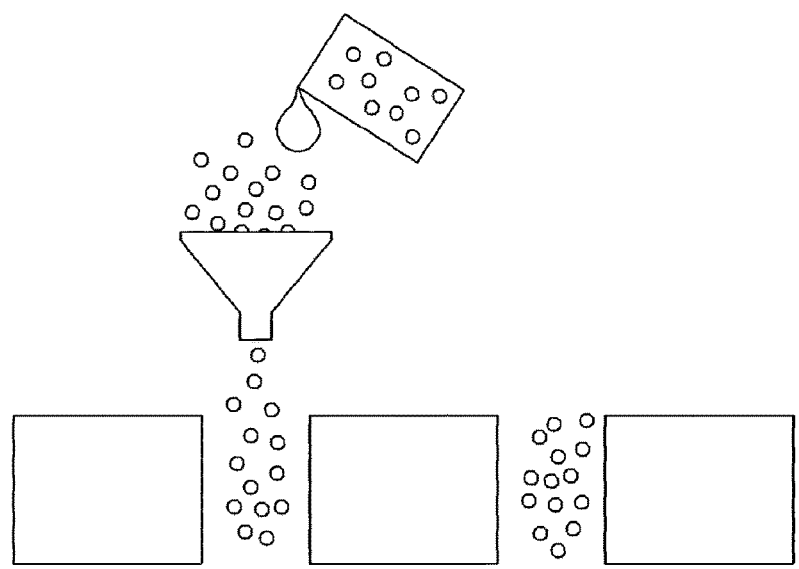
Figure 7E:
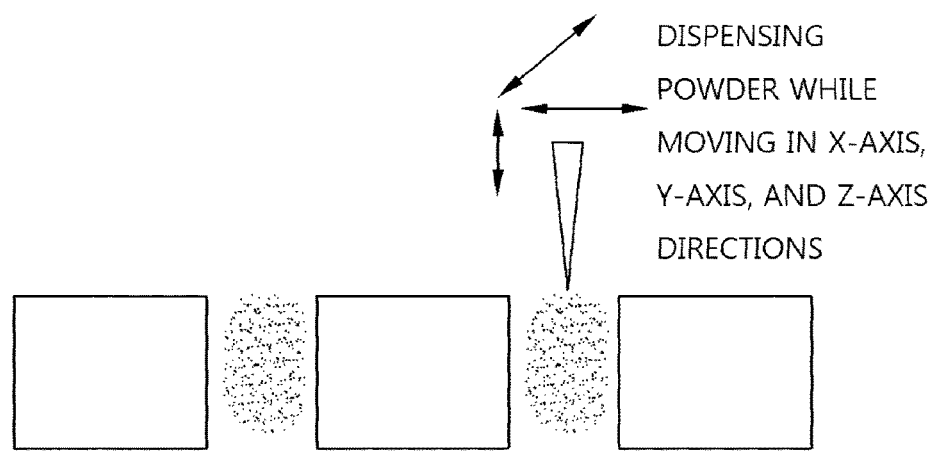
Figure 7F:
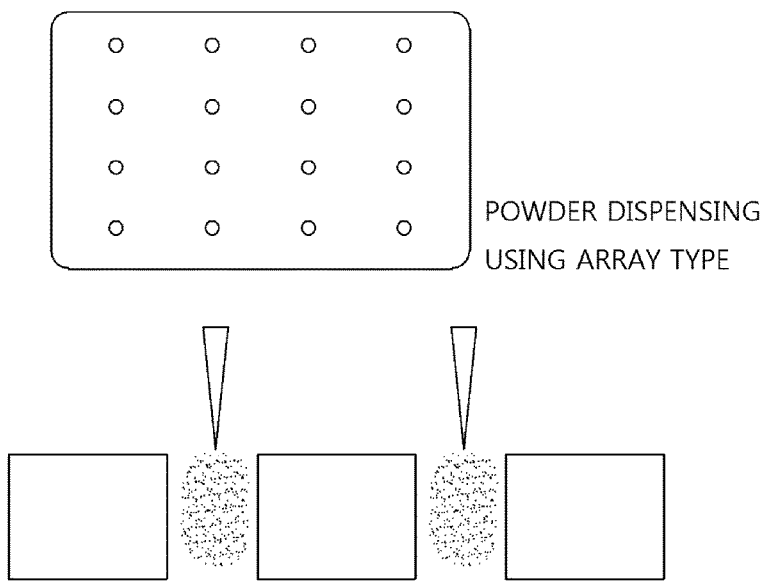
Figure 7G:
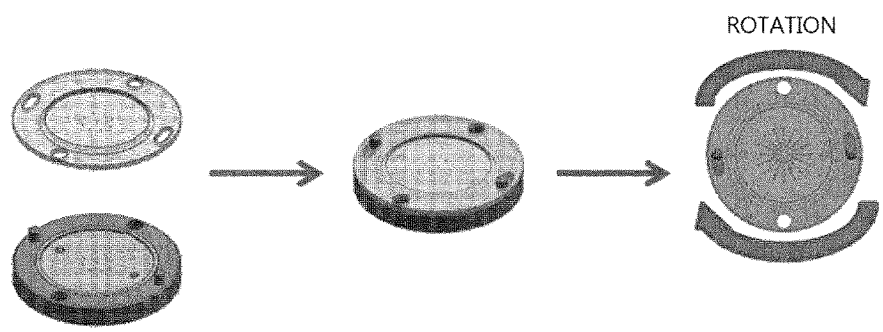

FIG. 7(b) illustrates an image of an upper end portion of a substrate with holes formed therein, each of which has a diameter of 375 µm and a length of 843 µm, is completely filled with a powder-type calcein sample, and a cross-sectional image thereof. FIG. 7(c) illustrates an image of an upper end portion of a substrate with holes formed therein, each of which has a diameter of 500 µm and a length of 860 µm, is completely filled with a powder-type calcein sample, and a cross-sectional image thereof.

Example 3

Figure 8D:
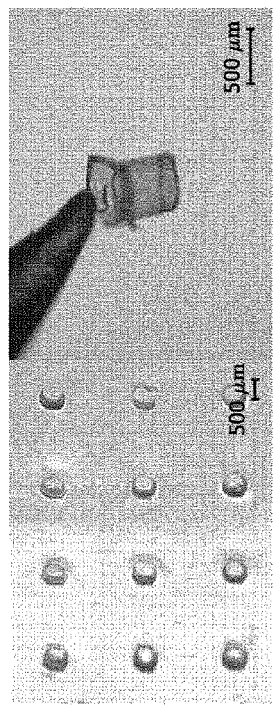

Molding of Microcontainer Film Structure in Substrate with Holes Formed Therein (1) A substrate with holes formed therein, each of which had a diameter of 500 µm and a length of 385 µm and a cylindrical shape, and was formed of PDMS, was filled with 10% w/v carboxymethylcellulose (CMC, low viscosity, Sigma-Aldrich) as a polymer composition sample, and then a solvent-removing process was performed twice, thereby molding a microcontainer film structure in the holes. A left-side image of FIG. 8(d) shows an upper end portion of the molding-completed microcontainer film structure, and a right-side image of FIG. 8(d) shows the microcontainer film structure separated from the substrate with holes formed therein. FIG. 8(e) illustrates a rectangular pillar-shaped microcontainer film structure separated from a PDMS mold for a substrate with rectangular pillar-shaped holes formed therein.

Figure 8F:
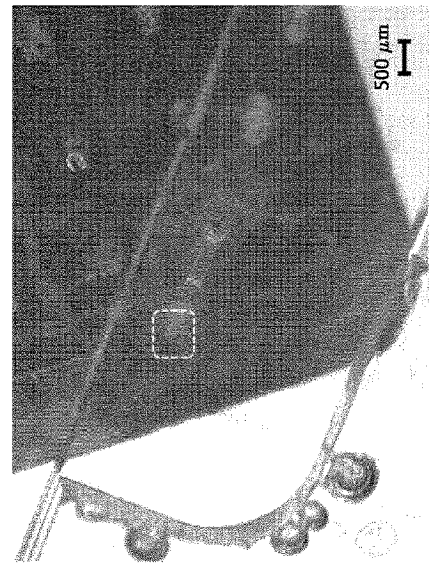
Figure 8E:
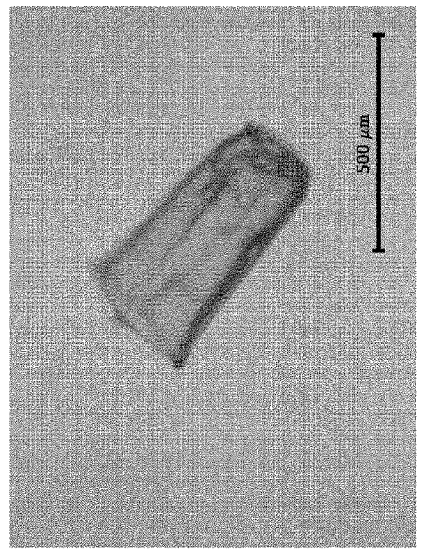

(2) A substrate with holes formed therein, each of which had a diameter of 258 µm and a length of 900 µm and a cylindrical shape, and was formed of PDMS, was filled with 10% w/v CMC (low viscosity, Sigma-Aldrich) as a polymer composition sample, and then a solvent-removing process was performed twice, thereby molding a microcontainer film structure in the holes (see FIG. 8(f)). The molded microcontainer film structure was physically separated from the substrate by using a cylindrical pillar template having a diameter of 258 µm and a length of 900 µm and formed of SUS, fabricated by a laser cutting technique.

Figure 8G:
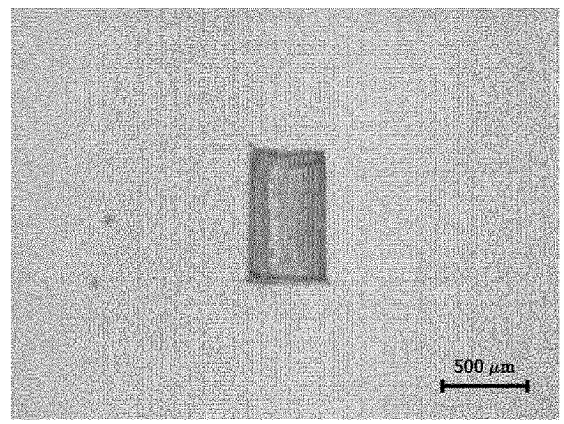
Figure 10D:
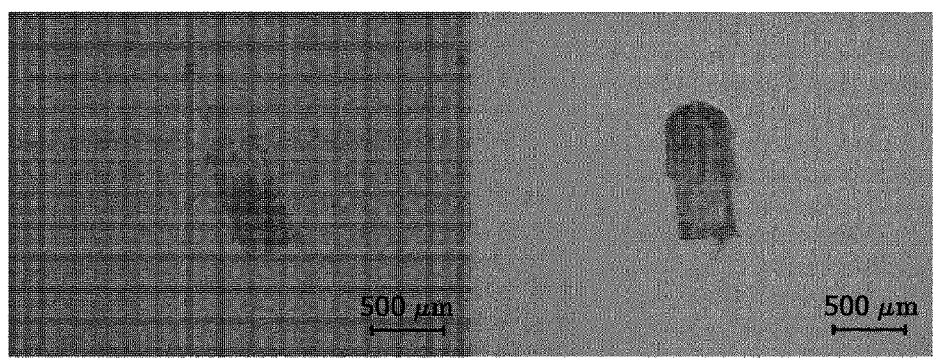

(3) A substrate with holes formed therein, each of which had a diameter of 425 µm and a length of 730 µm and a cylindrical shape, and was formed of PDMS, was filled with 10% w/v CMC (low viscosity, Sigma-Aldrich) as a polymer composition sample, and then a solvent-removing process was performed twice, thereby molding a microcontainer film structure in the holes (see FIG. 8(g)). Subsequently, a powder-type calcein (fluorescent dye, Sigma-Aldrich) sample was loaded in the molded microcontainers through vibration and cutting processes, and then the resulting structure was separated from the substrate with holes formed therein, formed of PDMS (see the left-side image of FIG. 10(d)). A second film structure prepared from a substrate with holes formed therein, each of which had a diameter of 450 µm and a length of 730 µm and a cylindrical shape, and was formed of PDMS, was aligned with the microcontainer film structure formed in the holes on which loading of the powder-type calcein sample had been completed, to be combined with each other, thereby finally molding a film structure in which upper and lower ends of the respective film structures were combined with each other (see the right-side image of FIG. 10(d)).

Figure 10E:
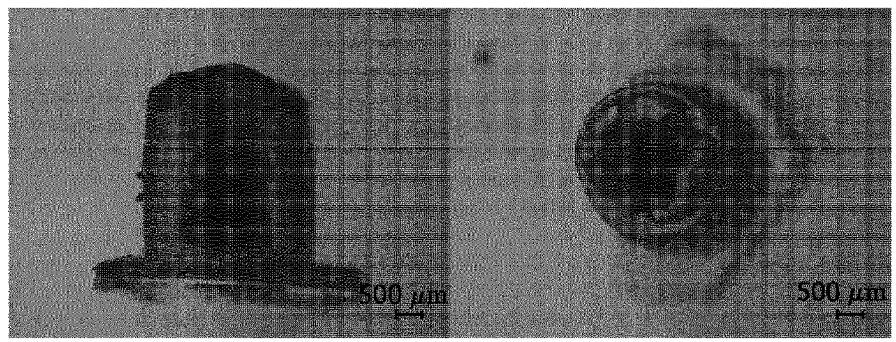

(4) A substrate with holes formed therein, each of which had a diameter of 2,800 µm and a length of 3,600 µm and a cylindrical shape, and was formed of PDMS, was filled with powder-type poly(D,L-lactide-co-glycolide) (PLGA, lactide:glycolide (65:35), Mw 40,000-75,000, Sigma-Aldrich), and then the resulting structure was heated to 100□. Cylindrical pillars having a diameter of 1,400 µm and formed of SUS were pressed onto the heated PLGA, and then the temperature of the resulting structure was decreased to 25□, thereby completing the molding of a microcontainer film structure formed of PLGA. The molded PLGA microcontainers were filled with a powder-type calcein (fluorescent dye, Sigma-Aldrich) sample and the resulting structure was separated from the substrate with holes formed therein, formed of PDMS (see FIG. 10(e)).

Example 4

Molding of Microcontainer Microstructure to be Inserted into Human Body

Figure 9H:
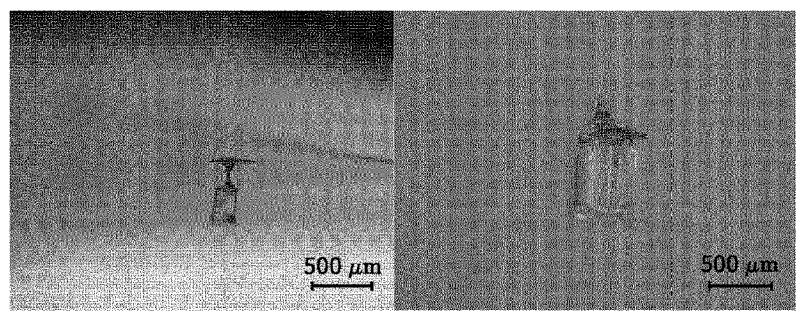

A substrate with holes formed therein, each of which had a diameter of 450 µm and a length of 730 µm and a cylindrical shape, and was formed of PDMS, was filled with a 10% w/v CMC polymer composition and dried, and the filling and drying processes were performed twice, thereby completing the formation of a cylindrical microcontainer film structure having a diameter of 450 µm and a length of 730 µm. Thereafter, 50% w/v hyaluronic acid (average Mw 28.5 kDa, PrimalHyal50, Soliance, Pomade, France) as a polymer composition was coated onto the microcontainer film structure, and then a separate microstructure was molded using tensile force (see FIG. 9(h)). The left-side image of FIG. 9(h) shows a result of molding a separate microstructure using tensile force, and, as in the right-side image of FIG. 9(h), an upper end portion of the separate microstructure was removed to mold a microcontainer microstructure to be inserted into the human body.

Example 5

Attachment of Microcontainer Film Structure to Flat Plate or Pillar

Figure 8H:
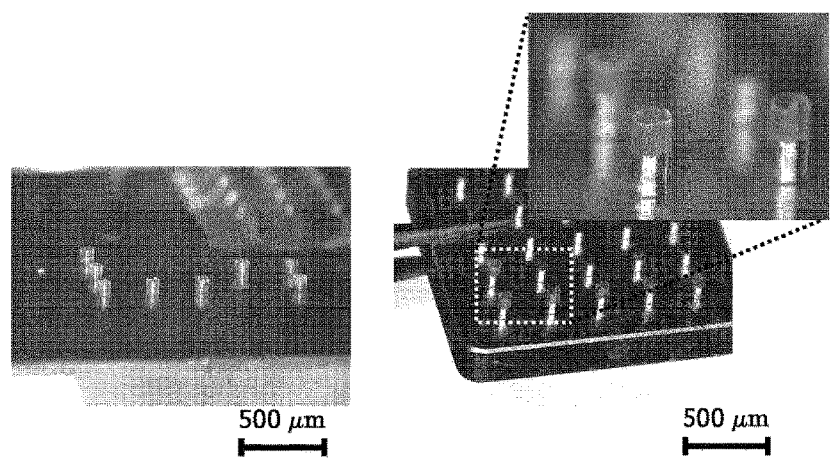

A substrate with holes formed therein, each of which had a diameter of 450 µm and a length of 400 µm, a cylindrical shape, and upper and lower openings, and was formed of PDMS, was filled with a 10% w/v CMC polymer composition sample including a fluorescent dye (calcein), and then a solvent-removing process was repeated twice, thereby molding a microcontainer film structure in the holes, and the microcontainer film structure was separated from the substrate and then attached to a flat plate or a pillar (see FIG. 8(h)). The left-side image of FIG. 8(h) shows a case in which the microcontainer film structure was attached to a flat plate, and the right-side image of FIG. 8(h) shows a case in which the microcontainer film structure was attached to pillars.

Figure 10F:
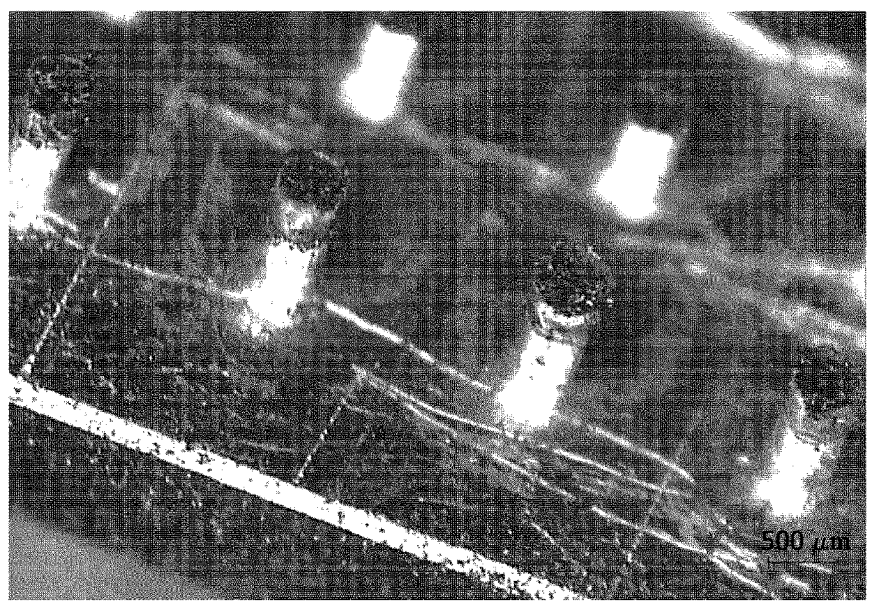

A powder-type dye (fluorescent dye: rhodamine B) was loaded in the microcontainers attached to pillars, and, as a result of dye quantification experimentation using a fluorescence spectrometer (LS55, Perkin Elmer, USA), the content of the dye was 30.1 µg per one capsule (see FIG. 10(f)).

Figure 10G:
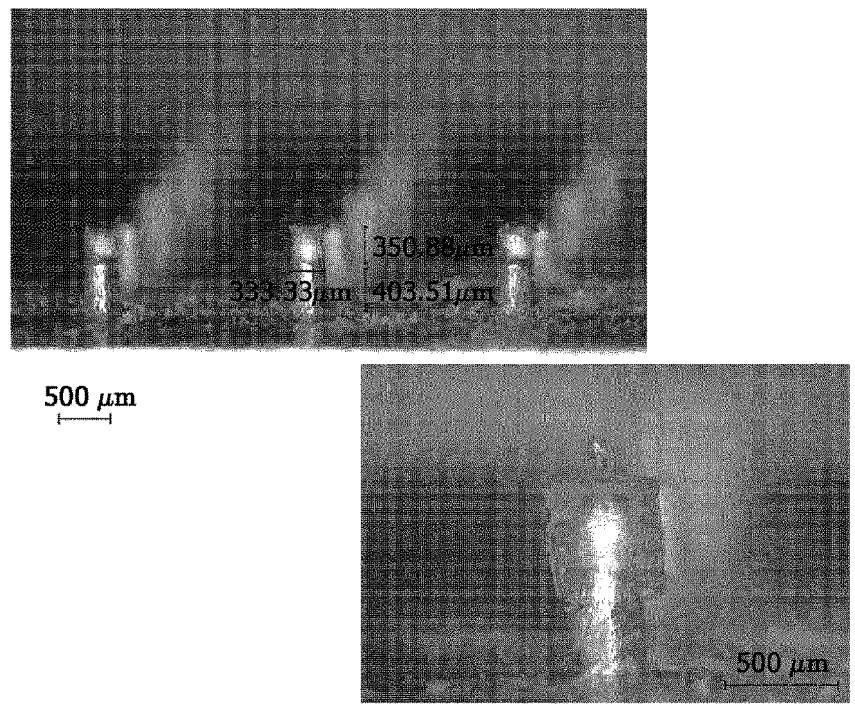

In addition, insulin (Human insulin, Sigma-Aldrich) was loaded in the microcontainers attached to pillars, and then combined with a second film structure, thereby obtaining a final film structure in which upper and lower ends of the respective film structures were combined with each other (see FIG. 10(g)).

While particular parts of the present invention have been described in detail, it is obvious to one of ordinary skill in the art that such detailed descriptions are only exemplary embodiments, and the embodiments set forth herein are not intended to limit the scope of the present invention. Thus, the actual scope of the present invention is construed as being defined by the appended claims and equivalents thereto.

The invention claimed is:

1. A microcontainer microstructure comprising:
   a substrate provided with a hole having an upper opening and a lower opening; and
   a microcontainer film structure formed in contact with an inner surface of the hole and comprising a container portion having a volume of 100um$^3$ to 1,000,000 um$^3$ and a sharp tip portion,
   wherein the container portion is loaded with a drug,
   wherein the container portion and the sharp tip portion of the microcontainer film structure are both configured to be inserted into a human body, and
   wherein the substrate is configured to contact a surface of the human body but not be inserted into the human body.

2. The microcontainer microstructure of claim 1, wherein the sharp tip portion is a polymer composition in contact with the microcontainer.

3. The microcontainer microstructure of claim 1, wherein the microcontainer microstructure comprises a second film structure formed in combination with the microcontainer film structure, to seal the drug.

4. The microcontainer microstructure of claim 3, wherein the microcontainer film structure and the second film structure are formed in an integrated form.

5. A method of manufacturing a microcontainer microstructure, the method comprising:
   (a) preparing a substrate provided with a hole having an upper opening and a lower opening; and
   (b) preparing a microcontainer film structure formed in contact with an inner surface of the hole and comprising a container portion having a volume of 100 um$^3$ to 1,000,000 um$^3$ and a sharp tip portion; and
   (c) loading a drug into the container portion,
   wherein the container portion and the sharp tip portion of the microcontainer film structure are both configured to be inserted into a human body, and wherein the substrate is configured to contact a surface of the human body but not be inserted into the human body.

6. The method of claim 5, further comprising, prior to process (b), filling the hole with a polymer composition or a thermoplastic polymer powder.

7. The method of claim 6, wherein, when the filling is performed using the polymer composition, in process (b) above, the preparing of the microcontainer film structure is performed by removing a solvent of the polymer composition.

8. The method of claim 6, wherein, when the filling is performed using the thermoplastic polymer powder, in process (b) above, the preparing of the microcontainer film structure is performed by plasticizing the thermoplastic polymer powder by heat and then curing the plasticized thermoplastic polymer powder.

9. The method of claim 5, wherein, in process (b), the sharp tip portion is formed by applying an outward force to a polymer composition formed on an upper portion of the microcontainer film structure, or is formed by additionally attaching a separate microstructure to an upper portion of the microcontainer film structure.

10. The method of claim 5, wherein the drug is sealed by a second film structure.

* * * * *

UNITED STATES PATENT AND TRADEMARK OFFICE
CERTIFICATE OF CORRECTION

PATENT NO.           : 10,441,545 B2                                     Page 1 of 1
APPLICATION NO.      : 15/536586
DATED                : October 15, 2019
INVENTOR(S)          : Hyung Il Jung et al.

It is certified that error appears in the above-identified patent and that said Letters Patent is hereby corrected as shown below:

On the Title Page

Item (71) Applicant:
Please delete "INDUSTRY-ACADEMIC COOPERATION FOUNDATION, YONSEI UNIVERSITY" and replace with -- JUVIC INC. --

Signed and Sealed this
Twenty-first Day of January, 2020

Andrei Iancu
*Director of the United States Patent and Trademark Office*